(12) United States Patent  (10) Patent No.: US 8,777,084 B2
Poo et al.  (45) Date of Patent: Jul. 15, 2014

(54) ANASTOMOSIS SYSTEM AND METHOD (71) Applicants: Ramon E. Poo, Miami, FL (US); Andreas G. Tzakis, Coconut Grove, FL (US)

(72) Inventors: Ramon E. Poo, Miami, FL (US); Andreas G. Tzakis, Coconut Grove, FL (US)

(73) Assignees: Biorep Technologies, Inc., Miami, FL (US); University of Miami, Miami, FL (US)

( * ) Notice: Subject to any disclaimer, the term of this patent is extended or adjusted under 35 U.S.C. 154(b) by 0 days.

(21) Appl. No.: 13/736,587

(22) Filed: Jan. 8, 2013

(65) Prior Publication Data

US 2013/0123817 A1 May 16, 2013

Related U.S. Application Data (62) Division of application No. 12/616,396, filed on Nov. 11, 2009, now Pat. No. 8,348,128.

(51) Int. Cl.
*A61B 17/068* (2006.01)
*A61B 17/064* (2006.01)
*A61B 17/11* (2006.01)

(52) U.S. Cl.
USPC ............ 227/179.1; 227/175.1; 227/176.1; 411/457; 606/139; 606/142; 606/153

(58) Field of Classification Search
USPC ............ 227/175.1, 176.1; 411/457; 606/139, 606/142, 153
See application file for complete search history.

(56) References Cited

U.S. PATENT DOCUMENTS

| | | | |
|---|---|---|---|
| 1,151,300 A | 8/1915 | Soresi | |
| 4,624,257 A | 11/1986 | Berggren et al. | |
| 5,976,159 A * | 11/1999 | Bolduc et al. | 606/142 |
| 6,966,917 B1 | 11/2005 | Suyker et al. | |
| 7,018,387 B2 | 3/2006 | Suyker et al. | |
| 7,223,274 B2 | 5/2007 | Vargas et al. | |
| 2002/0151916 A1* | 10/2002 | Muramatsu et al. | 606/158 |
| 2004/0092975 A1* | 5/2004 | Loshakove et al. | 606/153 |
| 2004/0172050 A1 | 9/2004 | Bolduc et al. | |
| 2004/0186489 A1 | 9/2004 | Lee | |
| 2004/0215221 A1 | 10/2004 | Suyker et al. | |
| 2004/0249399 A1 | 12/2004 | Cinquin et al. | |
| 2005/0067454 A1 | 3/2005 | Vresh et al. | |
| 2005/0149076 A1 | 7/2005 | Borghi et al. | |
| 2005/0182430 A1 | 8/2005 | Schenck | |
| 2005/0251179 A1 | 11/2005 | Vargas | |
| 2005/0288693 A1 | 12/2005 | Suyker et al. | |
| 2006/0004391 A1 | 1/2006 | Haverich et al. | |
| 2006/0004392 A1 | 1/2006 | Amarant | |
| 2006/0085017 A1 | 4/2006 | Borghi | |
| 2007/0049954 A1 | 3/2007 | Caty et al. | |
| 2007/0073317 A1 | 3/2007 | Tanaka | |
| 2007/0239180 A1 | 10/2007 | Kuester et al. | |
| 2011/0152862 A1 | 6/2011 | Brodbeck et al. | |

* cited by examiner

*Primary Examiner* — Michelle Lopez
(74) *Attorney, Agent, or Firm* — Novak Druce Connolly Bove + Quigg LLP (57) ABSTRACT

A system for performing anastomosis includes a plurality of staples, an annular staple support having structure for holding the staples, and a staple closing device for closing the staples to secure the canal ends together. A method for performing anastomosis and staples for performing anastomosis are also disclosed.

1 Claim, 9 Drawing Sheets

ANASTOMOSIS SYSTEM AND METHOD

This application claims priority to and is a divisional of U.S. patent application Ser. No. 12/616,396, filed Nov. 11, 2009, now U.S. Pat. No. 8,348,128, the entirety of which are incorporated herein by reference.

BACKGROUND OF THE INVENTION

Anastomosis is a surgical term for describing the joining of two hollow bodies, particularly blood and lymphatic vessels. Anastomosis can be end-to-end, as when the ends of a severed or damaged vessel are rejoined, or end-to-side, as when an end of a vessel is joined to the side of another vessel or hollow structure. The primary method for surgically anastomosing vessel ends has been the circumferential suture, in which a suture is hand applied around the ends of the two vessels. Circumferential suturing is a time consuming, exacting process. It is very important that the ends of the vessels be joined properly, as leakage or obstruction of the vessel lumen is possible, with potentially serious effects on the patient's health. The physical manipulation of the vessel that is necessary for circumferential suturing can also result in damage to the vessel ends, with resulting degradation of the anastomosed vessel.

Various mechanical methods have been proposed for performing end-to-end anastomosis without circumferential suturing. In one such method, mechanical anastomosis by eversion, the ends to be connected are turned inside out and then joined to each other by mechanical methods. Such techniques, however, have been known to damage the vessel walls or result in a reduced-flow lumen at the junction location.

SUMMARY OF THE INVENTION

A system for performing anastomosis includes a plurality of staples having an open and a closed position, and an annular staple support. The annular support defines an interior opening. The support holds the plurality of staples about the opening when the staples are in the open position, and releases the staples when the staples are in the closed position.

The annular staple support can have first and second annular portions, and engagement structure for securing the first and second annular portions together around a body canal. The engagement structure can include a hinge and/or a clasp. The support can have pins and the staples can have slots for engaging the pins to the staples. The slots can have a large diameter portion and a small diameter portion, and the pins can have a large diameter head. The head is smaller than the large diameter portion but larger than the small diameter portion, whereby the pin will retain the staple.

The annular portions can comprise ledge portions, where the ledge portions abut the staples when the staples are engaged to the support. A staple closing mechanism for closing the plurality of staples can be provided. The staple closing mechanism can have engagement surfaces which mate with the ledges of the support, whereby the staples will be closed simultaneously.

The staples can comprise at least one piercing projection. The staples can also comprise first and second sides connected at a junction to define an included space. The projection extends from one of the sides into the included space. The staples can have flexible portions permitting the sides to be moved toward one another.

The staples can be substantially circumferentially disposed in side-to-side alignment about the annular staple support. The closing mechanism can be a separate stapler device and can have a pair of jaws. Each of the jaws can comprise a concave portion dimensioned to substantially mate with a corresponding one of the annular portions.

A method for performing anastomosis can include the steps of: positioning an annular staple support defining an interior opening around a first canal end with the first canal end extending at least partially into the opening, the support retaining a plurality of staples circumferentially disposed around the opening; folding the first canal end back over the staple support so as to engage the staples; positioning the second canal end over the folded-back first canal end and the staples; closing the staples over the first canal end and the second canal end and detaching said staples from the staple support; and removing the staple support.

A staple for performing anastomosis includes first and second staple portions joined together at ends thereof so as to define an included space. The first staple portion includes structure for engaging a staple support. The second staple portion includes structure for engaging a canal. The structure for engaging a canal can include a projection for piercing the canal, the projection extending into the included space. The structure for engaging a staple support can comprises a slot. The slot can have a large diameter portion and a small diameter portion.

BRIEF DESCRIPTION OF THE DRAWINGS

There are shown in the drawings embodiments that are presently preferred it being understood, however, that the invention is not limited to the precise arrangements and instrumentalities shown, wherein.

DETAILED DESCRIPTION OF THE INVENTION

There is shown in FIGS. 1-6 an annular staple support 20 defining an opening 24. The staple support has structure for holding a plurality of staples 28 about the opening 24. The support 20 is positioned around the body canal with the body canal in the opening 24, and the support 20 is then removed from the body canal when the anastomosis has been completed. The support 20 can comprise two or more sections 30, 32 which can be connected and disconnected in some fashion to permit the placement or removal of the support 20 around a body canal. In the embodiment that is shown, the sections 30, 32 are pivotally joined at hinge pin 36 and secured by clasp members 40, 42. Other structure to connect and remove the support 20 from around the body canal is possible. Slots 46 or other structure such as protrusions can be provided to facilitate engagement by a tool such as forceps or pliers to position the support 20 around the body canal.

Figure 7:
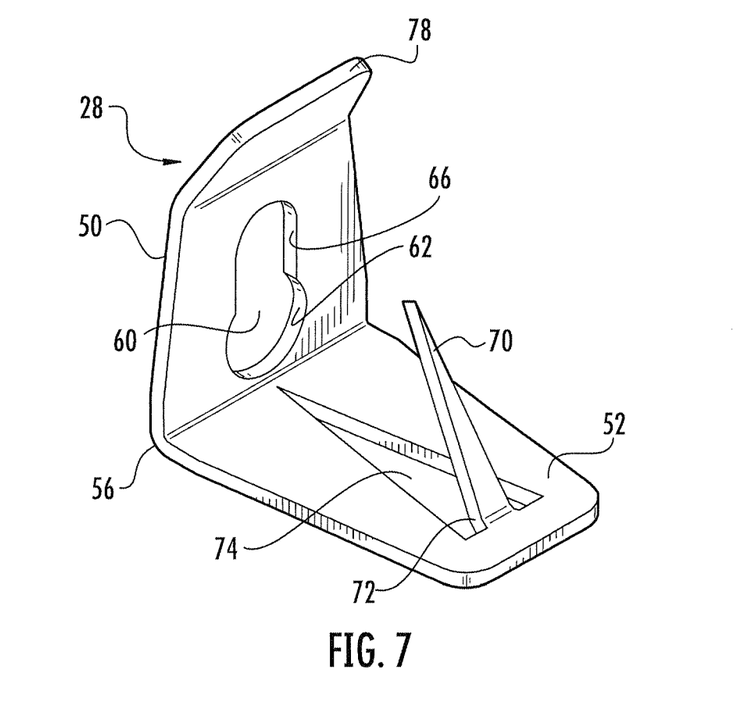
FIG. 7 is a perspective view of a staple according to the invention.
Figure 8:
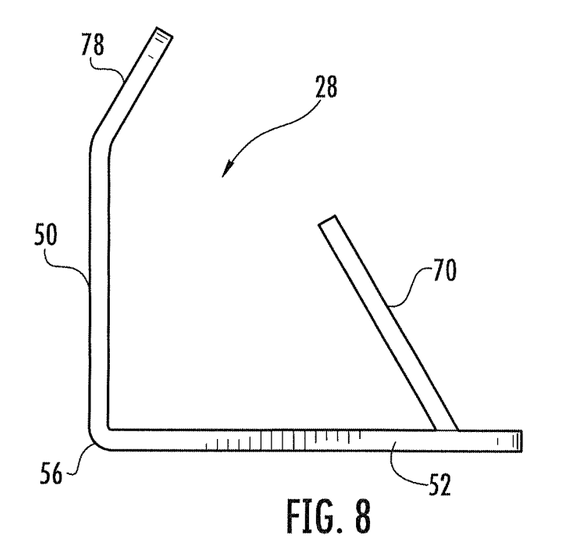
FIG. 8 is a side elevation.
Figure 9:
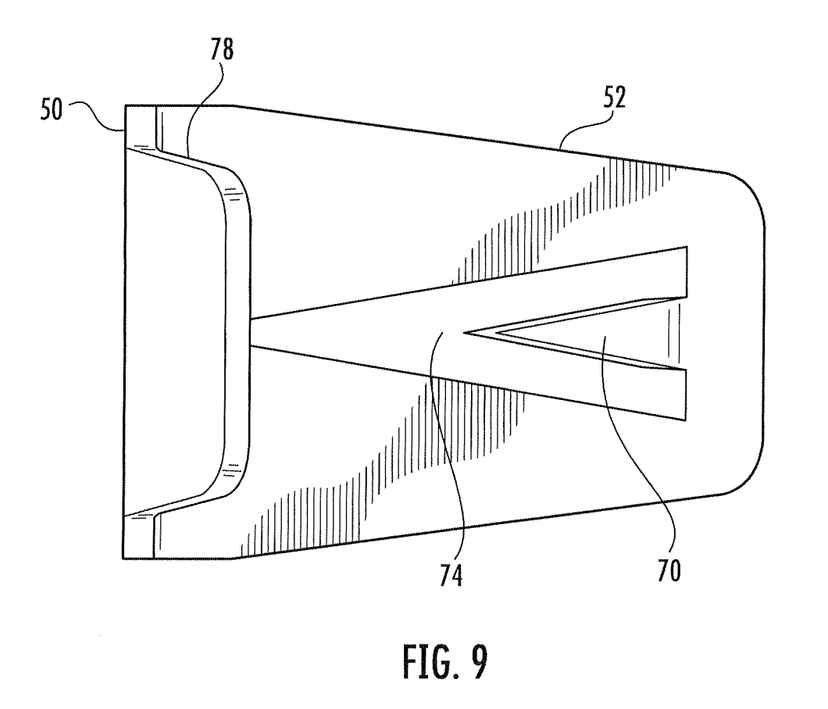
FIG. 9 is a top plan view.

The staples 28 are mounted to the support 20 such that they are retained on the support until they are engaged to the body canal during the anastomosis process. As shown in FIGS. 7-9, the staples 28 can have first and second sides 50, 52 joined together at a junction 56 and define an included space between the sides. The sides 50, 52 are shown joined at approximately a 90° angle, however other orientations are possible.

Figure 1:
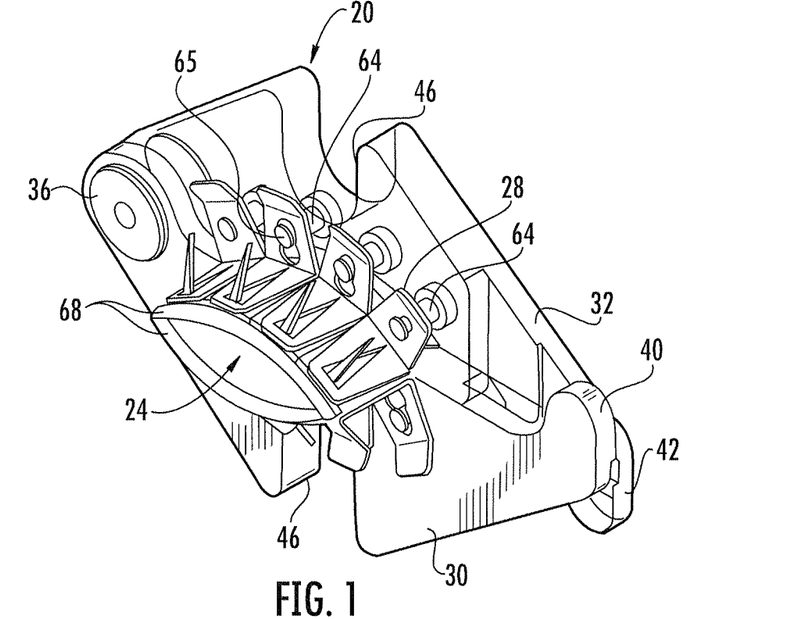
FIG. 1 is a perspective view of a staple support having a plurality of staples disposed thereon.
Figure 2:
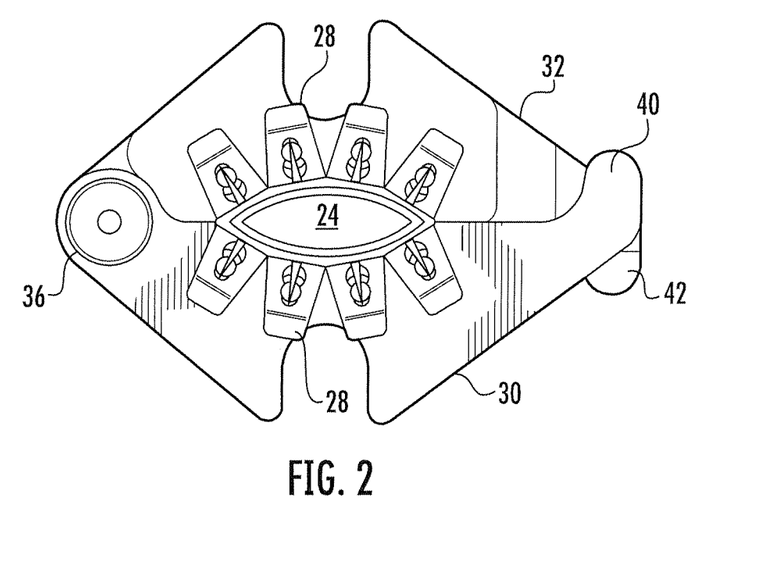
FIG. 2 is a front elevation.
Figure 3:
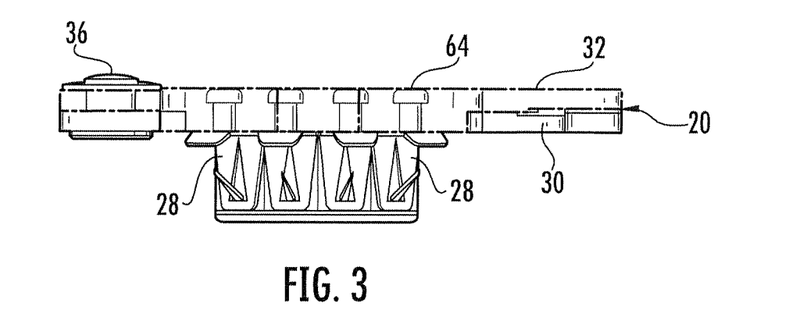
FIG. 3 is a top plan view.
Figure 4:
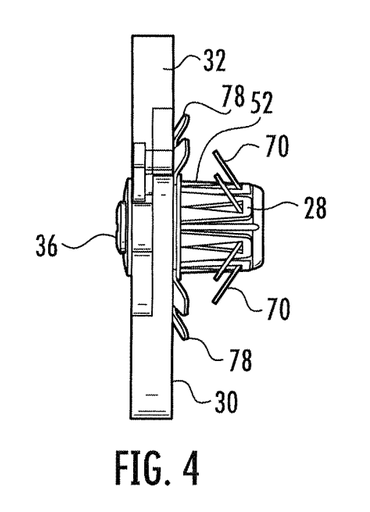
FIG. 4 is a side elevation.
Figure 5:
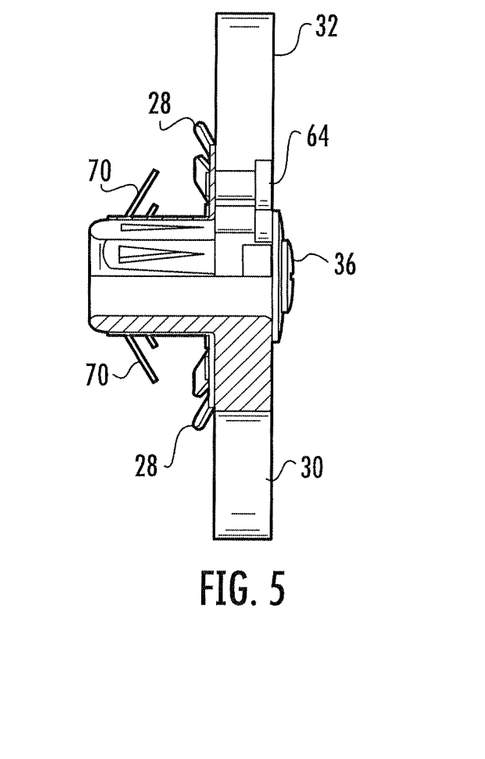
FIG. 5 is a cross section.
Figure 6:
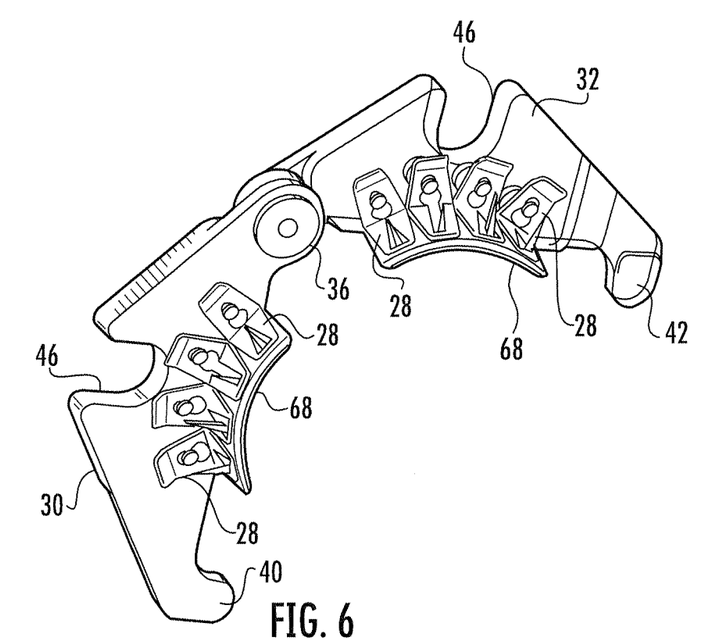
FIG. 6 is a perspective view in an open configuration.

Structure is provided to secure the staples 28 to the support 20. This structure can be provided on the support 20 or the staples 28, and in the embodiment that is shown this structure is cooperating structure on the staples 28 and on the support 20. At least one of the sides 50, 52 of the staples 28 has structure for detachably engaging the support 20. There are different structures that can be used to retain the staples 28 to the support 20. In the embodiment that is shown, the first side 50 of the staples 28 has keyed grooves 60 with a large diameter portion 62 and a smaller diameter portion 66 which are adapted to detachably engage cooperating protrusions or pins 64 on the support 20. The pins 64 can have a large diameter head 65 that is larger in diameter than the shaft of the pin, such that the head 65 will pass through the large diameter portion 62 but will not pass through the small diameter portion 66 of the grooves 60. This will retain the staple 28 when is positioned over the small diameter opening 66, as shown in FIG. 1. Other means for holding and releasing the staples, such as weak adhesives or alternative mechanical structures, are also possible.

The second side 52 of the staples 28 can be positioned adjacent ledge portions 68 of the support 20. The ledge portions 68 can be provided adjacent the opening 24. The ledge portions 68 can extend outwardly from the sections 30, 32 and can be substantially curved so as to conform to the opening 24. The ledge portions 68 provide a surface against which a force can be applied by the staple closing device to close the staples 28 and secure the ends of the body canal. The ledge portions 68 also serve to protect the body canal from damage during the anastomosis process. In one embodiment the ledge portions are substantially perpendicular to the sections 30, 32.

Each staple 28 has at least one projection for engaging the ends of the body canal. In one embodiment a piercing projection 70 is provided. The piercing projection 70 extends outwardly from one of the sides of the staple 28 such as the side 52 and extends toward the other side 50 such that when end portions of the body canal are placed between the sides 50, 52 the projection 70 will pierce and engage the end portions. The projection 70 can be formed in any suitable construction, and can in one embodiment be cut or stamped from the side 52 and bent outward at seam 72 to leave opening 74. Other configurations of the projection 70 are possible. More projections can be provided on a staple, and the projections can be positioned in different locations on the staple. Staples without projections are also possible A flange 78 can be provided at the free end of the side 50 to provide a surface which can be readily engaged by the staple closing device to close the staple 28 after the ends of the body canal have been engaged. The flange 78 will also serve to secure the tissue in the staple 28. The flange 78 can be formed by bending a portion of the free end of side 50 toward the side 52. Other structure for engaging the staple closing device is possible, for example, a protrusion formed on the staple surface.

Figure 10:
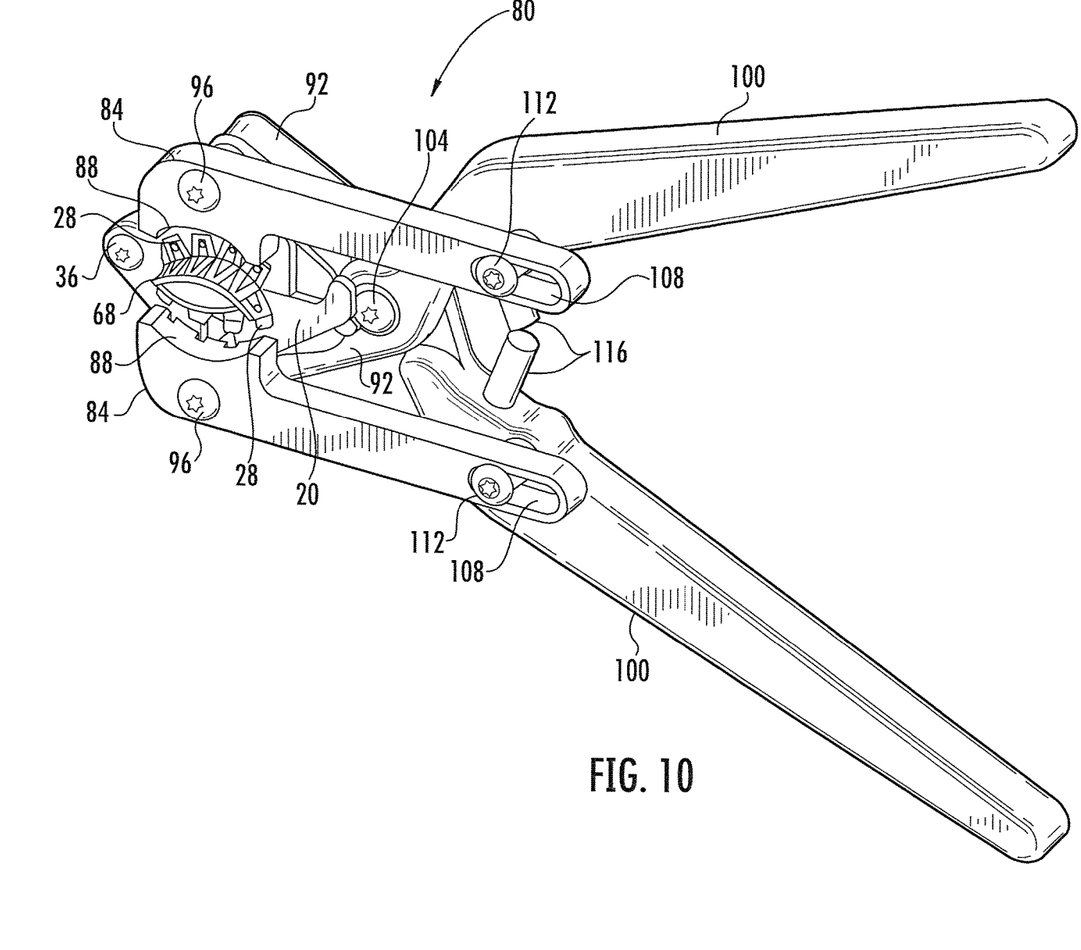
FIG. 10 is a perspective view of a stapling device positioned around the staple support and staples.

The staples 28 can be closed around the ends of the body canal by any suitable means. A special purpose staple closing device can be provided to close the staples. The staple closing device should preferably engage and close all of the staples in a single motion, in order to decrease the time required by the process and to provide a more even pressure around the canal during the anastomosis process. A suitable staple closing device 80 is shown in FIG. 10. The staple closing device 80 has a pair of cooperating jaws 84 with engagement surfaces 88. The engagement surfaces 88 are preferably shaped to substantially mate with ledge portions 68 such that when jaws 84 are closed, the staples 28 will be closed between the engagement surfaces 88 and ledge portions 68. The engagement surfaces 88 will engage the staples 28, such as at the flanges 78, to force the side 50 toward side 52 as the jaws 84 are closed. The staples 28 will thereby all be closed in the same motion, by a single operation of the staple closing device 80.

The jaws 84 of the stapler 80 can be operated by any suitable driving mechanism, including electrical or mechanical drive system. The embodiment shown in FIG. 10 has a mechanical, hand-operated drive system. The jaws 84 are pivotally connected to drive arms 92 by suitable structure such as pivot pins 96. The drive arms 92 can communicate with handles 100. A hinge pin 104 or other suitable structure pivotally connects the handles 100 and drive arms 92 in a scissor like fashion, such that manipulation of the handles 100 will move the drive arms 92 toward each other. Slots 108 in jaws 84 are engaged by pins 112 to handles 100 to limit pivoting of the jaws about pivot pins 96. Stops 116 can be provided on the handles 100 to limit movement of the handles 100, and thus the jaws 84, to a point which could result in damage to the staple 28, support 20, or body canal. It is also possible to construct an integrated staple support with a mechanism to close and release the staples, such that a separate stapler would not be necessary.

Figure 11:
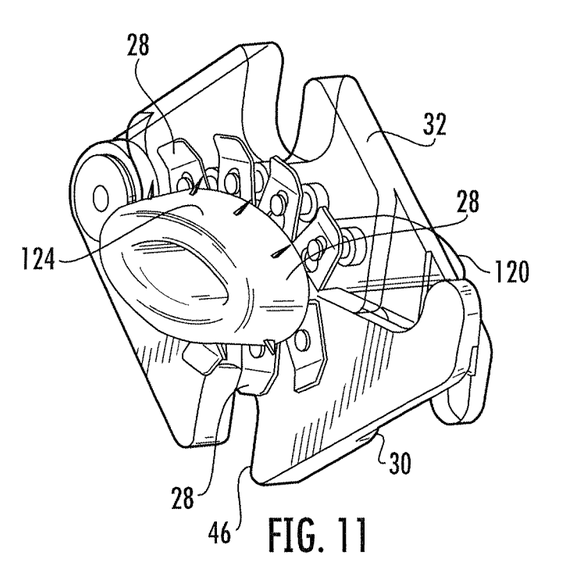
FIG. 11 is a perspective view of a first step of a method according to the invention.
Figure 12:
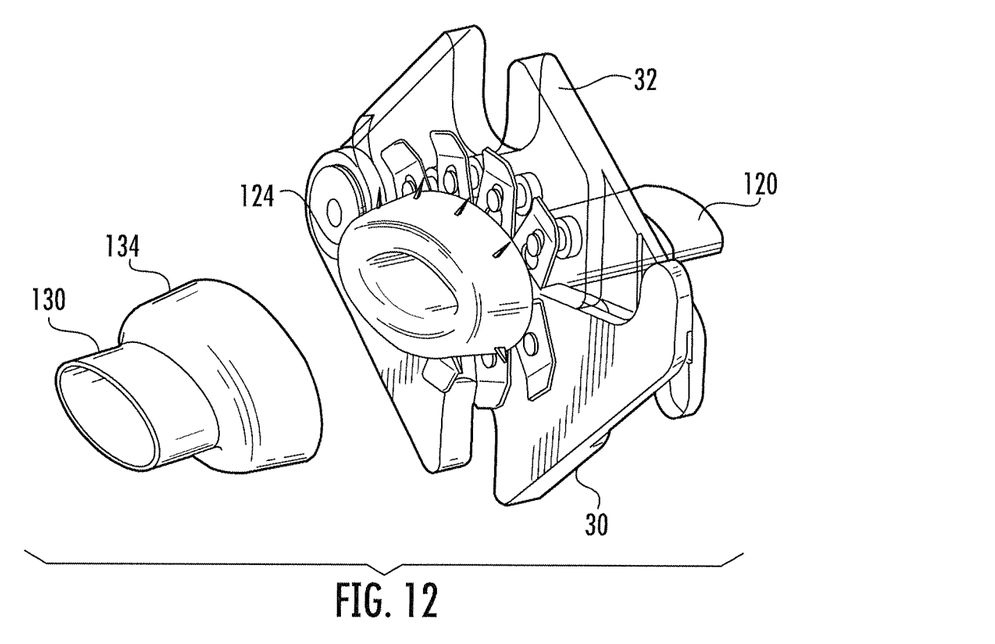
FIG. 12 is a perspective view of a second step.
Figure 13:
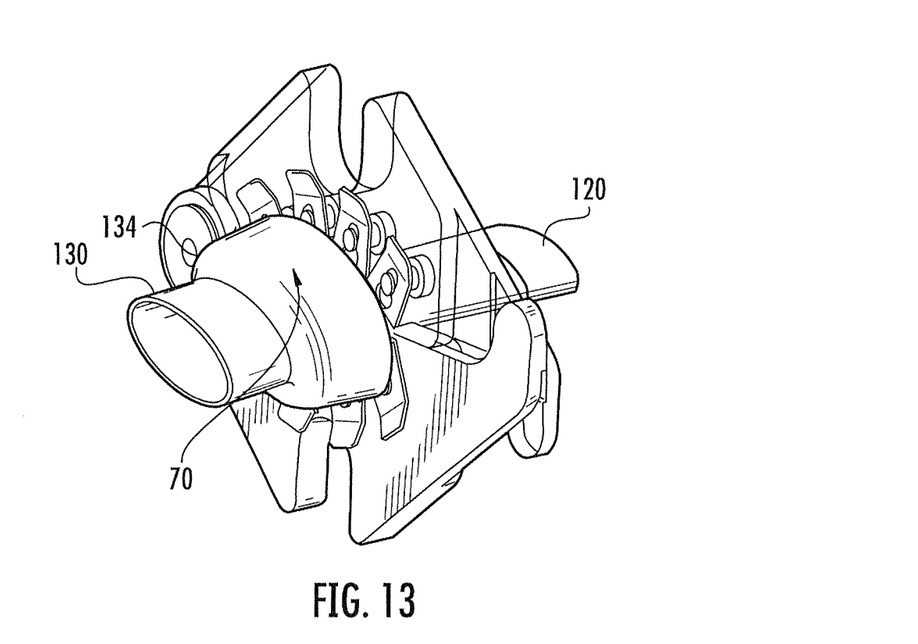
FIG. 13 is a perspective view of a third step.
Figure 14:
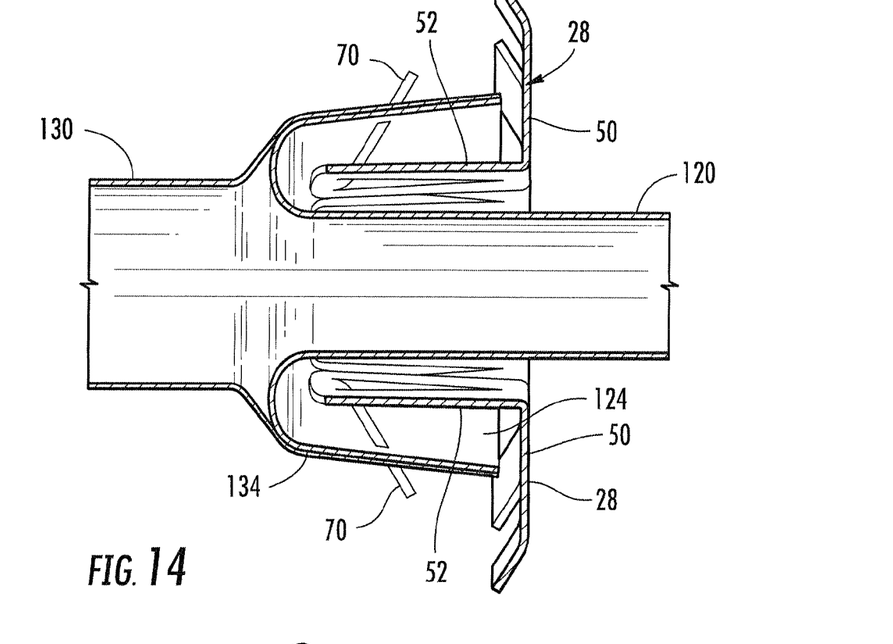
FIG. 14 is a cross section further illustrating the third step.
Figure 15:
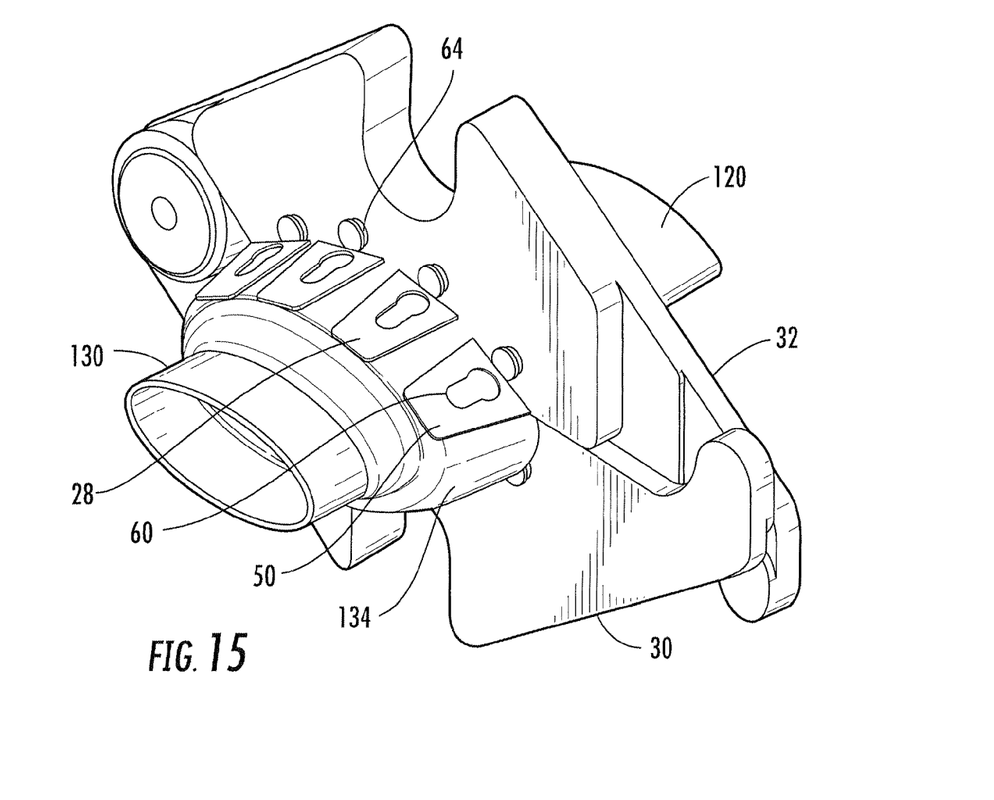
FIG. 15 is a perspective view of a fourth step.

An example of a process of performing anastomosis according to the invention is shown in FIGS. 11-17. The support 20 is provided with staples 28 positioned on pins 64, as shown in FIGS. 1-6. In FIG. 11 the sections 30, 32 are positioned around a first body canal portion 120. Slots 46 or other structure can be used to engage a tool to the support 20 to effect the placement and closing of the support 20 about a body canal. The free end 124 of the first body canal portion 120 is then folded back and engaged to the projections 70 or other engagement structure of the staples 28. The free end 134 of a second body canal portion 130 is then brought into position (FIG. 12), and then placed over the free end 124 of the first body canal portion 120 (FIG. 13). The free end 134 of the second body canal portion 130 is also engaged to the projections 70 as shown in FIG. 14. The staples 28 are then closed, as by the staple closing device shown in FIG. 10, which will force the staples 28 from the pins 64. This will secure the free end 124 of the first body canal portion 120 and the free end 134 of a second body canal portion 130 together, as shown in FIG. 15. The closing of the staples 28 can be substantially simultaneous, and accomplished by suitable structure such as the staple closing device 80. The support 20 can then be removed from its position around the body canal, as but disengaging the clasps 40, 42.

Figure 16:
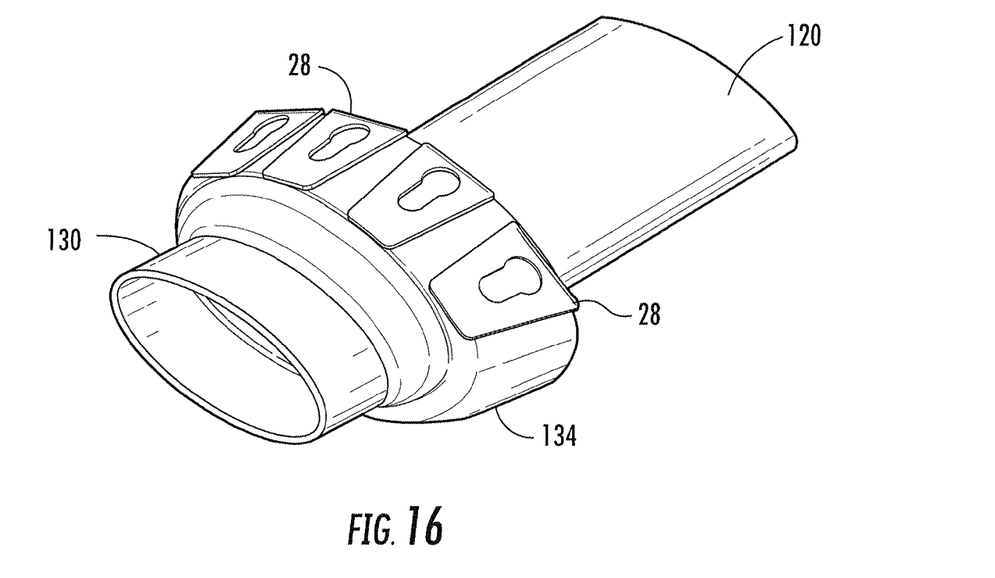
FIG. 16 is a perspective view of a body canal that has been anastomosed according to the invention.
Figure 17:
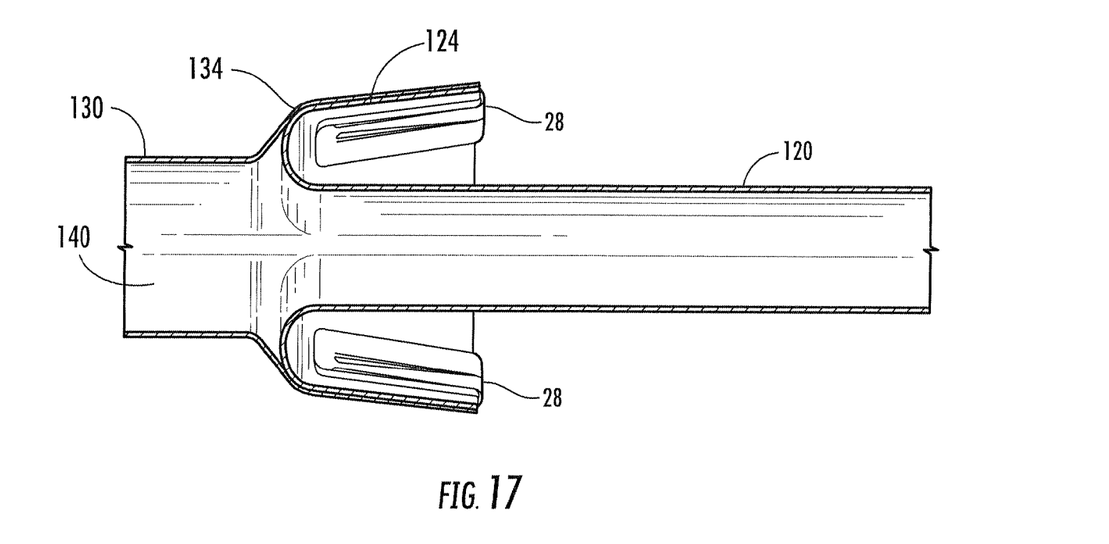
FIG. 17 is a cross section of a body canal that has been anastomosed according to the invention.

As shown in FIG. 16, the completed anastomosis junction site 144 has a profile which is comparable to that produced by currently used, more time-consuming anastomosis techniques, and will not interfere with repositioning the canal within the body. The completed anastomosis is depicted in FIG. 17 in cross section, where it is seen that the lumen 140 at the anastomosis site is substantially unchanged following the procedure.

The support 20 and staples 28 can be made in a variety of different sizes and shapes depending on the anastomosis procedure that is to be performed. The position of the ledge portions 68 and staples 28 must be such that the staples 28 are properly positioned adjacent the body canal so as to circumferentially engage the ends of the body canal. Smaller staples 28 allow more staples to be used, although more or fewer staples than those that are shown are possible.

This invention can be embodied in other specific forms without departing from the spirit or essential attributes thereof, and reference should be made to the appended claims, rather than to the foregoing specification, as indicating the scope of the invention.

We claim:

1. A staple for performing anastomosis, comprising:
   first and second staple portions joined together at ends thereof at a junction so as to define an included space;
   said first staple portion including structure for engaging a staple support, said structure comprising a slot, said slot comprising a large diameter portion and a small diameter portion, said slot being distanced from the junction;
   said second staple portion comprising structure for engaging a canal, wherein said structure for engaging a canal comprises a projection for piercing said canal, said projection extending into said included space.

* * * * *